US007618614B2

(12) United States Patent
Tada et al.

(10) Patent No.: US 7,618,614 B2
(45) Date of Patent: Nov. 17, 2009

(54) HYDROCEPHALUS TREATMENT

(75) Inventors: Tsuyoshi Tada, Matsumoto (JP);
Toshikazu Nakamura, Sakyou-ku (JP)

(73) Assignee: Shinshu TLO Co., Ltd., Nagano (JP)

( * ) Notice: Subject to any disclaimer, the term of this patent is extended or adjusted under 35 U.S.C. 154(b) by 332 days.

(21) Appl. No.: 10/579,297

(22) PCT Filed: Nov. 19, 2004

(86) PCT No.: PCT/IB2004/004459

§ 371 (c)(1),
(2), (4) Date: Jun. 26, 2006

(87) PCT Pub. No.: WO2006/000844

PCT Pub. Date: Jan. 5, 2006

(65) Prior Publication Data

US 2008/0194473 A1      Aug. 14, 2008

Related U.S. Application Data

(60) Provisional application No. 60/524,094, filed on Nov. 20, 2003.

(51) Int. Cl.
*A61K 49/00* (2006.01)
*C12P 21/06* (2006.01)
*A61K 38/24* (2006.01)
*C12P 15/09* (2006.01)
(52) U.S. Cl. .................. 424/9.1; 435/69.1; 435/69.4; 530/399
(58) Field of Classification Search .................. None
See application file for complete search history.

(56) References Cited

U.S. PATENT DOCUMENTS 5,840,311 A    11/1998  Nakamura et al.
2002/0013265 A1   1/2002  Schwartz

FOREIGN PATENT DOCUMENTS

JP    A 7-300426    11/1995

OTHER PUBLICATIONS

Tsuzuki et al., Neurological Research, 23(4): 417-424, Jun. 2001.*
Tsuzuki et al. Acta Neurochirurgica Supplement, 76:311-316, 2000.*
Fukumizu et al., Pediatric Neurology, 13(3):230-234, published Oct. 1995.*
Y. Tsuboi et al., "Hepatocyte Growth Factor in Cerebrospinal Fluid in Neurologic Disease", ACTA Neurologica Scandinavica, vol. 106, pp. 99-103, 2002.
Tsuyoshi Tada et al., "Intraventricular Administration of Hepatocyte Growth Factor Treats Mouse Communicating Hydrocephalus Induced by Transforming Growth Fact β1", Neurobiology of Disease, vol. 21, pp. 576-586, 2006.

Di Rocco et al., "Anatomo-Clinical Correlations in Normotensive Hydrocephalus," Journal of the Neurological Sciences, vol. 33, pp. 437-452, 1977.
Yasargil et al., "Hydrocephalus following spontaneous subarachnoid hemorrhage, Clinical features and treatment," J. Neurosurg., vol. 39, pp. 474-479, Oct. 1973.
Almuneef et al., "Childhood Bacterial Meningitis in Saudi Arabia," Journal of Infection, vol. 36, pp. 157-160, 1998.
Daoud et al., "Indications and Benefits of Computed Tomography in Childhood Bacterial Meningitis," Journal of Tropical Pediatrics, vol. 44, pp. 167-169, Jun. 1998.
Gomes et al., "Prognosis of Bacterial Meningitis in Children," Arq Neuropsiquiatr, vol. 54, No. 3, pp. 407-411, 1996.
Grimwood et al., "Adverse Outcomes of Bacterial Meningitis in School-Age Survivors," Pediatrics, vol. 95, No. 5, pp. 646-656, May 1995.
Youmans, J.R., Chapter 36; "Hydrocephalus in Childhood," Neurological Surgery, Fourth Edition, vol. 2, W.B. Saunders Company, Philadelphia, pp. 890-926, 1996.
Graff-Radford et al., "Factors Associated With Hydrocephalus After Subarachnoid Hemorrhage, A Report of the Cooperative Aneurysm Study," Arch Neurol, vol. 46, pp. 744-752, Jul. 1989.
Pfister et al., "Spectrum of Complications During Bacterial Meningitis in Adults, Results of a Prospective Clinical Study," Arch. Neurol, vol. 50, No. 6, pp. 575-581, Jun. 1993.
Lobato et al., Hydrocephalus in cerebral cysticercosis, Pathogenic and therapeutic considerations, J. Neurosurg., vol. 55, pp. 786-793, Nov. 1981.
Torvik et al., "Transitory Block of the Arachnoid Granulations Following Subarachnoid Haemorrhage: A Postmortem Study," Acta Neurochirurgica, vol. 41, pp. 137-146, 1978.
Akai et al., "Normal Pressure Hydrocephalus, Neuropathological Study," Acta Pathol. Jpn., vol. 37, No. 1, pp. 97-110, 1987.
Massicotte et al., "Human arachnoid villi response to subarachnoid hemorrhage: possible relationship to chronic hydrocephalus," J. Neurosurg., vol. 91, pp. 80-84, Jul. 1999.
Motohashi et al., Subarachnoid Haemorrhage Induced Proliferation of Leptomeningeal Cells and Deposition of Extracellular Matrices in the Arachnoid Granulations and Subarachnoid Space, Acta Neurochir, vol. 136, pp. 88-91, 1995.
Kang et al., "Long-term follow-up of shunting therapy," Child's Nerv Syst, vol. 15, pp. 711-717, 1999.
Sgouros et al., "Long-Term Complications of Hydrocephalus," Pediatr Neurosurg, vol. 23, pp. 127-132, 1995.
Del Bigio, "Epidemiology and Direct Economic Impact of Hydrocephalus: A Community Based Study," Can J. Neurol. Sci., vol. 25, pp. 123-126, 1998.
Nakamura et al., "Molecular cloning and expression of human hepatocyte growth factor," Nature, vol. 342, pp. 440-443, Nov. 23, 1989.
Miyazawa et al., "Molecular Cloning and Sequence Analysis of the cDNA for a Human Serine Protease Responsible for Activation of Hepatocyte Growth Factor," The Journal of Biological Chemistry, vol. 268, No. 14, pp. 10024-10028, 1993.

(Continued)

*Primary Examiner*—John D Ulm
*Assistant Examiner*—Stacey MacFarlane
(74) *Attorney, Agent, or Firm*—Oliff & Berridge, PLC

(57) ABSTRACT

A method and compound for treatment of hydrocephalus is presented. Hepatocyte growth factor (HGF) is administered intraventricularly.

4 Claims, 8 Drawing Sheets

OTHER PUBLICATIONS

Dohi et al., "Hepatocyte Growth Factor Attenuates Collagen Accumulation in a Murine Model of Pulmonary Fibrosis," Am J Respir Crit Care Med, vol. 162, pp. 2302-2307, 2000.

Matsuda et al., "Hepatocyte Growth Factor Suppresses the Onset of Liver Cirrhosis and Abrogates Lethal Hepatic Dysfunction in Rats," J. Biochem, vol. 118, No. 3, pp. 643-649, 1995.

Fujimoto, "Hepatology: Microcirculation and Pathogenesis of Alcoholic Liver Injury, Gene therapy for liver cirrhosis," Journal of Gastroenterology and Hepatology, vol. 15 (Suppl.), pp. D33-D36, 2000.

Vargas et al., "Hepatocyte growth factor in renal failure: Promise and reality," Kidney International, vol. 57, pp. 1426-1436, 2000.

Rosen et al., "Scatter Factor and the *c-Met* Receptor: A Paradigm for Mesenchymal/Epithelial Interaction," The Journal of Cell Biology, vol. 127, No. 6, Part 2, pp. 1783-1787, Dec. 1994.

Brinkmann et al., "Hepatocyte Growth Factor/Scatter Factor Induces a Variety of Tissue-Specific Morphogenic Programs In Epithelial Cells," The Journal of Cell Biology, vol. 131, No. 6, Part 1, pp. 1573-1586, Dec. 1995.

Ohmichi et al., "Hepatocyte growth factor (HGF) acts as a mesenchyme-derived morphogenic factor during fetal lung development," Development, vol. 125, pp. 1315-1324, 1998.

Matsumoto et al., "Hepatocyte growth factor in renal regeneration, renal disease and potential therapeutics," Current Opinion in Nephrololgy and Hypertension, vol. 9, pp. 395-402, 2000.

Flood et al., "Transforming Growth Factor-$\beta$1 in the Cerebrospinal Fluid of Patients with Subarachnoid Hemorrhage: Titers Derived From Exogenous and Endogenous Sources," Journal of Cerebral Blood Flow and Metabolism, vol. 21, pp. 157-162, 2001.

Takizawa et al., "Inflammatory cytokine cascade released by leukocytes in cerebrospinal fluid after subarachnoid hemorrhage," Neurological Research, vol. 23, pp. 724-730, Oct. 2001.

Ossege et al., "Expression of tumor necrosis factor-$\alpha$ and transforming growth factor-$\beta$1 in cerebrospinal fluid cells in meningitis," Journal of the Neurological Sciences, vol. 144, pp. 1-13, 1996.

Hunag et al., "Level of transforming growth factor beta 1 is elevated in cerebrospinal fluid of children with acute bacterial meningitis," J. Neurol, vol. 244, pp. 634-638, 1997.

Galbreath et al., "Overexpression of TGF-$\beta$1 in the Central Nervous System of Transgenic Mice Results in Hydrocephalus," Journal of Neuropathology and Experimental Neurology, vol. 54, No. 3, pp. 339-349, May 1995.

Wyss-Coray et al., "Increased Central Nervous System Production of Extracellular Matrix Components and Development of Hydrocephalus in Transgenic Mice Overexpressing Transforming Growth Factor-$\beta$1," American Journal of Pathology, vol. 147, No. 1, pp. 53-67, Jul. 1995.

Cohen et al., "Characterization of a model of hydrocephalus in transgenic mice," J. Neurosurg., vol. 91, pp. 978-988, Dec. 1999.

Stoddart, Jr. et al., "Transgenic Mice with a Mutated Collagen Promoter Display Normal Response During Bleomycin-Induced Fibrosis and Possess Neurological Abnormalities," Journal of Cellular Biochemistry, vol. 77, pp. 135-148, 2000.

Hayashi et al., "Chronological Changes of Cerebral Ventricular Size in a Transgenic Model of Hydrocephalus," Pediatric Neurosurgery, vol. 33, No. 4, pp. 182-187, 2000.

Morris, "Spatial Localization Does Not Require the Presence of Local Cues," Learning and Motivation, vol. 12, pp. 239-260, 1981.

Sarnyai et al., "Impaired hippocampal-dependent learning and functional abnormalities in the hippocampus in mice lacking serotonin$_{1A}$ receptors," PNAS, vol. 97, No. 26, pp. 14731-14736, Dec. 19, 2000.

Cruz et al., "Observations on the use of medetomidine/ketamine and its reversal with atipamezole for chemical restraint in the mouse," Laboratory Animals, vol. 32, No. 1, pp. 18-22, Jun. 9, 1997.

Kern et al., "Concentrations of Hepatocyte Growth Factor in Cerebrospinal Fluid Under Normal and Different Pathological Conditions," Cytokine, vol. 14, No. 3, pp. 170-176, May 7, 2001.

Weller et al., "Pathways of Fluid Drainage from the Brain—Morphological Aspects and Immunological Significance in Rat and Man," Brain Pathology, vol. 2, pp. 277-284, 1992.

Kida et al., "CSF drains directly from the subarachnoid space into nasal lymphatics in the rat. Anatomy, histology and immunological significance," Neuropathology and Applied Neurobiology, vol. 19, pp. 480-488, 1993.

Moinuddin et al., "Study of cerebrospinal fluid flow dynamics in TGF-$\beta$1 induced chronic hydrocephalic mice," Neurological Research, vol. 22, pp. 215-222, Mar. 2000.

Nitta et al., "Ultramicroscopic Structures of the Leptomeninx of Mice with Communicating Hydrocephalus Induced by Human Recombinant Transforming Growth Factor-$\beta$1," Neurol Med Chir (Tokyo), vol. 38, pp. 819-825, 1998.

Taniyama et al., "Potential Contribution of a Novel Antifibrotic Factor, Hepatocyte Growth Factor, to Prevention of Myocardial Fibrosis by Angiotensin II Blockade in Cardiomyopathic Hamsters," Circulation, 2000, vol. 102, pp. 246-252, http://circ.ahajournals.org/cgi/content/full/102/2/246, Jan. 31, 2006.

Adams et al., "Symptomatic Occult Hydrocephalus with 'Normal' Cerebrospinal-Fluid Pressure," The New England Journal of Medicine, vol. 273, No. 3, pp. 117-126, Jul. 15, 1965.

Tada et al., "Induction of communicating hydrocephalus in mice by intrathecal injection of human recombinant transforming growth factor-$\beta$1," Journal of Neuroimmunology, vol. 50, pp. 153-158, 1994.

Kitazawa et al., "Elevation of Transforming Growth Factor-$\beta$1 Level in Cerebrospinal Fluid of Patients With Communicating Hydrocephalus After Subarachnoid Hemorrhage," Stroke, vol. 25, No. 7, pp. 1400-1404, 1994.

Sajanti et al., "Transient increase in procollagen propeptides in the CSF after subarachnoid hemorrhage," Neurology, vol. 55, pp. 359-363, 2000.

Miyazawa et al., "Protection of Hippocampal Neurons From Ischemia-Induced Delayed Neuronal Death by Hepatocyte Growth Factor: A Novel Neurotrophic Factor," Journal of Cerebral Blood Flow and Metabolism, vol. 18, No. 4, pp. 345-348.

\* cited by examiner

Morris water maze before and 4 weeks after HGF treatment

No.114 Sham-operated

No.35 Hydrocephalic

No.31 HGF treated

HYDROCEPHALUS TREATMENT

BACKGROUND OF THE INVENTION

1. Field of Technology

The present invention relates to a treatment for hydrocephalus. More particularly, the present invention relates to the intraventricular administration of a growth factor to treat hydrocephalus.

2. Description of Related Art

Hydrocephalus sometimes follows meningitis and intracranial hemorrhage, especially after bacterial meningitis or subarachnoid hemorrhage (SAH) (Di Rocco, C., at al, J. Neurol Sci, 1977. 33(3): p. 437-452; Yasargil, M. G., et al., J Neurosurg, 1973. 39(4): p. 474-479; Almuneef, M., et al., J Infect, 1998. 36(2): p. 157-160; Dacud, A. S., et al., J Trop Pediatr., 1998. 44(3): p. 167-169; Gomes, I., et al., Arq Neuropsiquiatr, 1996. 54(3): p. 407-411; Grimwood, K., et al., Pediatrics, 1995. 95(5): p. 646-656). Patients with hydrocephalus present elevated intracranial pressure signs such as headache and vomiting in the acute phase, and show character changes in behavior and decline in school performance in the chronic phase (Youmans, J. R., ed. Neurological Surgery, fourth edition ed. C. Saint Rose. Vol. 2. 1996, W.B. Saunders Company: Philadelphia, p. 890-926). Elderly patients with hydrocephalus present memory disturbance, gait disturbance and urinary incontinence without headache; this Is widely known as "normal pressure hydrocephalus" (Adams, R. D., et al., The New England Journal Of Medicine, 1965. 273(1965): p. 117-126; Graff-Radford, N. R., et al., Arch Neurol, 1989. 46(7): p. 744-752; Pfister, H. W., Feiden, W., and Einhaupl, K. M., Arch Neurol, 1993. 50(6): p. 575-581). Reversible dementia is one of the best known symptoms of normal pressure hydrocephalus in humans (Youmans, J. R., ed. Neurological Surgery, fourth edition ed. C. Saint Rose. Vol. 2. 1996, W.B. Saunders Company: Philadelphia, p. 890-926).

In communicating hydrocephalus, communication is established between the ventricles and a drainage cavity such as the peritoneum (Youmans, J. R., ed. Neurological Surgery, fourth edition ed. C. Saint Rose. Vol. 2. 1996, W.B. Saunders Company: Philadelphia, p. 890-926), in contrast to obstructive hydrocephalus, which involves compression or obliteration of the route of cerebrospinal fluid (CSF) by a brain tumor or membrane. The causes of communicating hydrocephalus have not yet been clarified. Histological evidence of fibrosis of arachnoid villi and subarachnoid space has been found in many autopsy studies (Lobato, R. D., et al., J. Neurosurg, 1981. 55(5): p. 786-793; Torvik, A., Bhatia, R., and Murthy, V. S., Acto Neurochir (Wien), 1978. 41(1-3): p. 137-146; Akai, K., et al., Acta Pathol Jpn, 1987. 37(1): p. 97-110). Some autopsy reports suggest that a possible cause is proliferation of arachnoid cap cells of arachnoid granules, but there is no conclusive evidence that this is specific to hydrocephalic patients (Massicotte, E. M. and Del Bigio, M. R., J Neurosurg, 1999. 91(1): p. 80-84; Motohashi, O., et al., Acta Neurochir (Wien), 1995. 136(1-2): p. 88-91). Therefore, it is reasonable to speculate that fibrosis of the subarachnoid space and arachnoid villi causes a mild pressure gradient across the CSF flow route, and that this is a major factor in development of hydrocephalus. Currently, shunting is the only definitive therapy for communicating hydrocephalus. However, there are many potential complications for people who undergo shunting surgery (Kang, J. K. and Lee, I. W., Child's Nervous System, 1999. 15(11-12): p. 711-717). The parents of patients shunted in infancy should be made aware of the possible problems with shunting. Even with patients who have been stable for a long period, significant clinical problems may arise during adulthood. These problems require replacement of the shunt system Joon-Ki and I. W. Lee, Child's Nervous System, 1999. 15: p. 711-717). It is essential for neurosurgeons to follow shunted patients for a long time (Sgouros, S., et al., Pediatr Neurosurg, 1995. 23(3): p. 127-132), and the social cost of maintaining such patients in good condition can be considerable (Del Bigio, M. R., Can J Neurol Sci, 1998. 25(2): p. 123-126).

Hepatocyte growth factor (HGF) was originally identified and cloned as a potent mitogen for mature hepatocytes (Nakamura, T. et al., Nature, 1989. 342(6248): p. 440-443; Miyazawa, K. et al., J. Biol Chem, 1993. 268(14): p. 10024-10028). It has a potent ability to reduce fibrosis in many organs, and it is expected to become a therapeutic material for various fibrotic diseases, including pulmonary fibrosis, liver cirrhosis and acute renal failure (Dohi, M. et al., Am J Respir Crit Care Med, 2000. 162(6): p. 2302-2307; Matsuda, Y. et al., J Biochem (Tokyo), 1995. 118(3): p. 643-649; Fujimoto, J., J Gastroenterol Hepatol, 2000. 15 Suppl: p. D33-D36; Vargas, G. A., Hoeflich, A., and Jehle, P. M., Kidney Int, 2000. 57(4): p. 1426-1436). HGF is a multi-potent growth factor that has mitogenic, motogenic and morphogenic effects on various epithelial cells and is produced by mesenchyme. It acts upon epithelial tissues in liver, kidney and lung, and counteracts the fibrosis-inducing effect of TGF-$\beta$1 (Rosen, E. M., Nigam, S. K. and Goldberg, I. D., J Cell Biol, 1994. 127(6 Pt 2): p. 1783-1787; Brinkmann, V. et al., J Cell Biol, 1995. 131(6 Pt 1): p. 1573-1586; Ohmichi, H. et al., Development, 1998. 125(7): p. 1315-1324; Matsumoto, K., Mizuno, S. and Nakamura, T., Curr Opin Nephrol Hypertens, 2000. 9(4): p. 395-402). Neutralization of HGF by antibody leads to acceleration of renal failure/fibrosis, and administration of exogenous HGF leads to marked attenuation of renal failure/fibrosis (Matsumoto, K., Mizuno, S. and Nakamura, T., Curr Opin Nephrol Hypertens, 2000. 9(4): p. 395-402).

The present invention is directed to the aforementioned problems. An object of the present invention is to provide an improved treatment for hydrocephalus using hepatocyte growth factor (HGF). To this end, a model of hydrocephalus in mice by administering human recombinant (hr) transforming growth factor $\beta$1 (TGF-$\beta$1) (Tada, T., Kanaji, M. and Kobayashi, S. J Neuroimmunol, 1994. 50(2): p. 153-158) has been tested; such hydrocephalic mice present with clear disturbance of spatial learning ability in a water maze test. In the present hydrocephalus model, learning disturbance is reversible, which is very unique for such models, and is similar to human normal pressure hydrocephalus. The present invention therefore presents an alternative to shunting as a therapy for hydrocephalus.

SUMMARY OF THE INVENTION

To achieve the foregoing objects, the present invention provides a method of treatment for hydrocephalus in an animal, comprising the step of intraventricular administration of hepatocyte growth factor (HGF).

The present invention further provides a compound useful for the treatment of hydrocephalus, comprising HGF and a suitable carrier. In a preferred embodiment, the HGF is human recombinant HGF (hrHGF).

DESCRIPTION OF THE PREFERRED EMBODIMENTS

Figure 1:
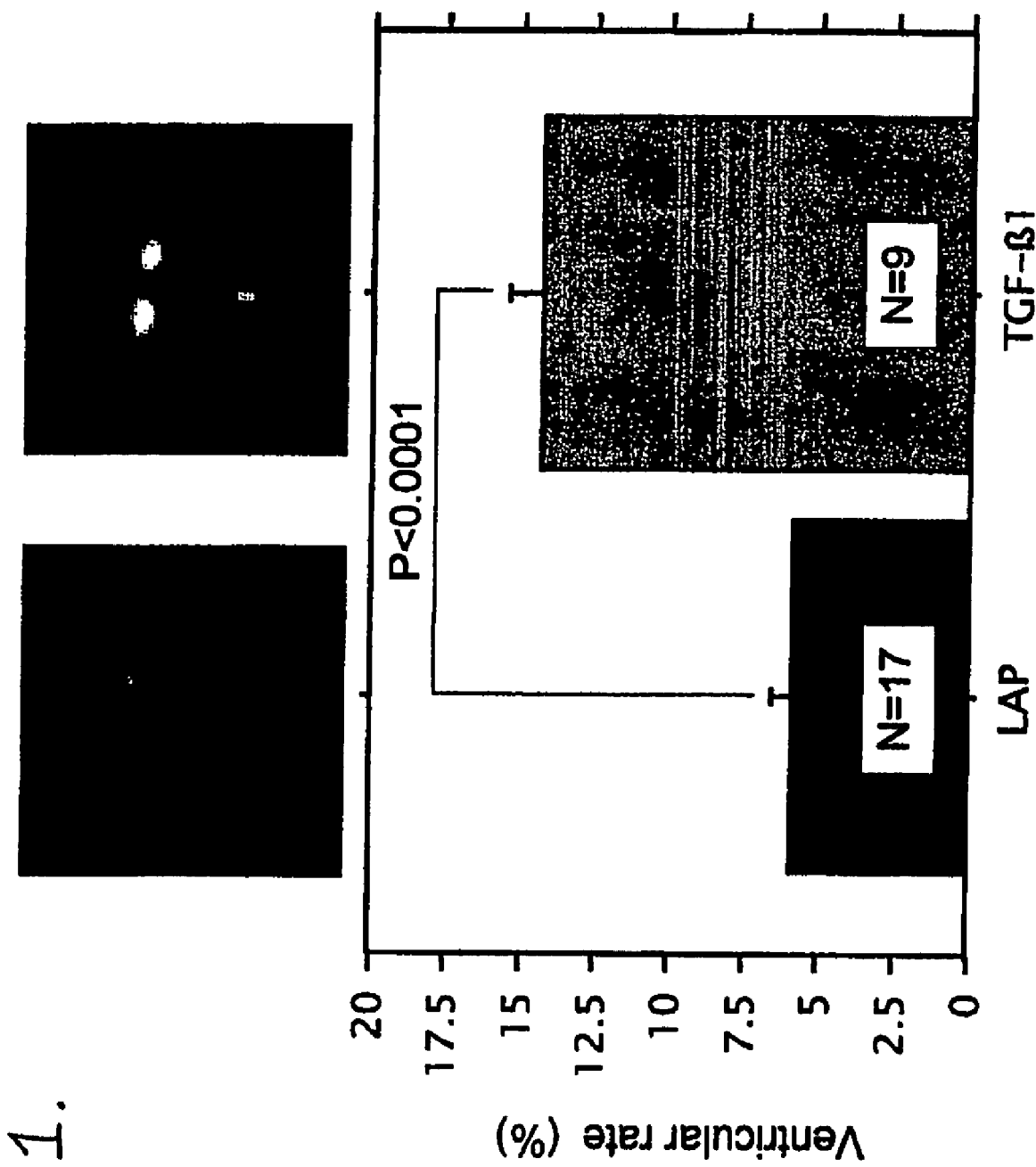
FIG. 1 depicts magnetic resonance imaging MRI brain images of human recombinant (hr) TGF-$\beta$1-injected mice.

The present invention provides a method of treating hydrocephalus in an animal, comprising the step of intraventricular administration of hepatocyte growth factor (HGF). In a preferred embodiment, the HGF is human recombinant HGF (hrHGF). The present invention further provides a pharmaceutical compound useful for the treatment of hydrocephalus, comprising HGF and a pharmaceutically acceptable carrier. "Pharmaceutically acceptable carrier" refers to any carrier, diluent, excipient, wetting agent, buffering agent, suspending agent, lubricating agent, adjuvant, vehicle, or delivery system that would be suitable for use in a pharmaceutical composition. In a most preferred embodiment, the HGF of the compound is hrHGF.

By way of example and not limitation, the following examples are provided.

Animals and Reagents

Human recombinant transforming growth factor β1 (hrTGF-β1) and human recombinant latency associated peptide (LAP) were purchased from R & D systems, Inc. (Minneapolis, Minn.). Human recombinant HGF (hrHGF) was prepared by the inventors, Matsumoto and Nakamura at Osaka University School of Medicine, Osaka, Japan. Pregnant C57BL/6 mice were purchased from Japan SLC Inc. (Shizuoka, Japan); ten-day-old mice were used in this experiment.

Mice were housed in a polycarbonate cage in the Shinshu University Animal House, and were fed with a commercial diet (MF, Oriental Yeast Co. Ltd., Tokyo, Japan). All mice were kept under a 12:12 hour dark-light cycle (lights on at 9:00 am). The room was kept at 24±2° C. and 55±10% relative humidity. This study was carried out in accordance with the Guidelines for Animal Experimentation of the Shinshu University School of Medicine.

hrTGF-β1-induced hydrocephalus: An animal model of communicating hydrocephalus

Levels of TGF-β1 level in CSF doubles after subarachnoid hemorrhage, as shown by enzyme-linked immunoabsorbent assay (ELISA). The first peak occurs within a day of ictus, and involves release of TGF-β1 from platelets. The second peak occurs in the second week after the ictus, and involves release of TGF-β1 from neutrophils and lymphocytes in CSF and choroid plexus (Flood, C. et al., J Cereb Blood Flow Metab, 2001. 21(2): p. 157-162; Takizawa, T. et al., Neurol Res, 2001. 23(7): p. 724-730). In the second week after ictus, TGF-β1 levels are higher in CSF of patients with hydrocephalus than in patients without hydrocephalus (Kitazawa, K. and Tada, T., Stroke, 1994. 25(7): p. 1400-1404). Up to 10 weeks after ictus, levels of the metabolites of collagen synthesis (type I and type III procollagen) in CSF are also higher in patients with hydrocephalus (Sajanti, J., Heikkinen, E. and Majamaa, K., Neurology, 2000. 55(3): p. 359-363). The TGF-β level is also elevated in CSF of patients with bacterial meningitis. Some clinical findings suggest that elevated TGF level is one of the causes of hydrocephalus following bacterial meningitis (Ossege, L. M. et al., J Neurol Sci, 1996. 144(1-2): p. 1-13; Huang, C. C. et al., J Neurol, 1997. 244(10): p. 634-638). The above observations strongly suggest that TGF-β1 plays an important role in generating hydrocephalus after meningitis and subarachnoid hemorrhage.

In 1994, the inventors experimentally administered hrTGF-β1 into the head of C57BL/6 mice, resulting in a hydrocephalic condition. The lateral ventricles continued to dilate until 6 weeks after administration of hrTGF-β1, and remained dilated until 12 weeks after administration (Tada, T., Kanaji, M. and Kobayashi, S. J Neuroimmunol, 1994. 50(2): p. 153-158). Electron microscopy revealed abundant deposition of collagen fibers in the inter-cellular space of the leptomeninx (Nitta, J and Tada, T., Neurol Med Chir (Tokyo), 1998. 38(12): p. 819-824). Transgenic mice expressing TGF-β1 gene develop communicating hydrocephalus, and extracellular matrix protein is deposited in their meninges (Galbreath, E. et al., J Neuropathol Exp Neurol, 1995. 54(3): p. 339-349; Wyss-Coray, T. et al., Am J Pathol, 1995. 147(1): p. 53-67; Cohen, A. R. et al., J Neurosurg, 1999. 91(6): p. 978-988; Stoddart, J. J. Jr. et al., J Cell Biochem, 2000. 77(1): p. 135-148; Hayashi, N., Leifer, D. W. and Cohen, A. R., Pediatr Neurosurg, 2000. 33(4): p. 182-187). Because these transgenic mice die soon after birth, they are difficult to use in experiments.

In the present study, we also observed CSF stasis using CT cisternography was also observed. The intraventricularly injected contrast material clearly stayed in the interhemispheric fissure at least 120 minutes after injection in the hydrocephalic mice. In normal mice, contrast material had left the interhemispheric fissure within 15 minutes, and the whole head (including the surrounding soft tissues) was well enhanced with recycled contrast material at 120 minutes after injection. These results strongly suggest that intermeningeal fibrosis is a main cause of hrTGF-β1-induced hydrocephalus.

In addition to morphological examination, memory function of TGF-β1-injected mice was assessed. Reversible dementia is a characteristic symptom of normal pressure hydrocephalus in elderly patients. Shunted normal pressure hydrocephalus patients recover well. To estimate the learning ability of mice with hrTGF-β1-induced hydrocephalus, a Morris water maze test is used, which indicates that about half of the TGF-β1-injected mice had disturbed spatial learning. The disturbed spatial learning of the hydrocephalic mice continued for at least 4 weeks after the first Morris water maze. Because of these observations, hrTGF-β1-injected mice with disturbed spatial learning and ventricular dilatation are characterized hereinafter as hydrocephalic.

Morris Water Maze

Spatial learning ability was examined with a transfer test in a modified Morris water maze, as previously described (Morris, R. G. M., Learning and motivation, 1981. 12: p. 239-260; Samyai, Z. et al., Proc Natl Acad Sci USA, 2000. 97(26): p. 14731-14736). Briefly, a clear plastic platform (diameter, 8 cm) was placed in a quadrant of a pool (diameter, 88 cm), and submerged 1 cm below the water surface. The quadrant in which the platform was placed and the remaining quadrants, clockwise from the former, were designated (A), (B), (C) and (D), respectively. Training consisted of 12 trials each day for 3 consecutive days. The mouse was allowed 60 seconds to search for the platform in the training. Once the mouse located the platform, it was permitted to remain on it for 30 seconds. Spatial learning ability was examined after the last training session. Mice were required to swim in the pool without the platform for 60 seconds. The swimming was recorded by a video camera, and the time the mice spent swimming in each quadrant was measured as the score.

Anesthesia

Animals were sedated by intraperitoneal injection of a mixture of ketamine hydrochloride (2.5 mg/mouse) and medetomidine (0.025 mg/mouse). To reverse the anesthesia, antipamezole hydrochloride (0.125 mg/mouse) was injected (Cruz, J. I., Loste, J. M. and Burzaco, O. H., Lab Anim, 1998. 32(1): p. 18-22).

Magnetic Resonance Imaging

Mouse heads were examined with a 1.5-tesla whole-body magnetic resonance (MR) imager (Signa Advantage, General Electric, Milwaukee, Wis.), using standard gradient hardware with a round surface coil (diameter, 3 inches). T2-weighted images were obtained with sequences (coronal plane; slice, 0.5 cm; TE, 90 msec; TR, 2000 msec). Images including the thalamus were used for comparison, because these images had the widest ventricular space and were common in our MR imaging series. NIH Image (ver.1.61) was used to calculate the pixels representing the whole coronal section of the brain and the total high-intensity pixels representing the bilateral lateral ventricles and the upper and the lower parts of third ventricle. The rate of high-intensity pixels among total pixels of the coronal section was defined as the ventricular size.

Preparation of Hydrocephalic Mice

As previously described, 10-day old mice were injected in the subcranium with hrTGF-β1 (60 ng/head) (Tada, T., Kanaji, M. and Kobayashi, S. J Neuroimmunol, 1994. 50(2): p. 153-158). Spatial learning ability of all hrTGF-β1-injected mice was examined with the Morris water maze in the animal house 6 weeks after injection. Ventricular size of mice with disturbed spatial learning was examined with MRI. Mice with disturbed spatial learning and dilated ventricles were designated as hydrocephalic.

Administration of hrHGF hrHGF was administered intraventricularly instead of systemically, because hrHGF does not pass the blood-CSF barrier (Kern, M. A. et al., Cytokine, 2001. 14(3): p. 170-176). The dosage was based on results of a previous study, in which 30 µg of hrHGF was administered in the lateral ventricle of gerbil brain using an osmotic pump (Miyazawa, T. et al., J Cereb Blood Flow Metab, 1998. 18(4): p. 345-348). Administration of HGF in rats for several weeks did not have negative side effects that would rule out application of HGF in cases of liver disease or other organ diseases (Matsuda, Y. et al., J Biochem (Tokyo), 1995. 118(3): p. 643-649).

A total of 30 µg of hrHGF per mouse using 7-day and 14-day infusion type osmotic mini-pumps was continuously administered. hrHGF was administered at 30 µg per mouse with two models of osmotic mini-pump (Model 1007D, 1002; Alza Co, Palo Alto, Calif.). Model 1007D and Model 1002 can continuously infuse the contents for 7 and 14 days, respectively. The mouse was placed in a stereotaxic frame (Model 900, Pembroke Pines, Fla.). A hole was made in the skull, 0.6 mm caudal from the coronal suture and 1 mm lateral from the midline. An L-shaped 28-gauge stainless steel cannula was inserted intracranially at a depth of 4 mm. Each cannula was connected to an osmotic pump, filled with 30 µg of HGF in 0.1% BSA-PBS solution, in the back via a catheter tube. The sham-operated mice were injected with 0.1% BSA-PBS only, using the Model 1007D osmotic pump. The pump was immediately removed after the hrHGF administration.

Ink Passage Test

Although the features of hrTGF-β1-induced hydrocephalus in mice are very similar to those of human hydrocephalus, rodents and humans have very different CSF drainage systems. Rat CSF mainly drains to deep cervical lymph nodes via nasal lymphatics, whereas, in humans, CSF mainly drains to arachnoid villi (Weller, R. O., Kida, S. and Zhang, E. T., Brain Pathol, 1992. 2(4): p. 277-284; Kida, S., Pantazis, A. and Weller, R. O., Neuropathol Appl Neurobiol, 1993. 19(6): p. 480-488). A simple method for detecting disturbance of CSF flow by measuring the time it takes for the deep cervical lymph nodes to turn black after injection of ink has been developed by the present inventors (Moinuddin, S. M. and Tada, T., Neurol Res, 2000. 22(2): p. 215-222). This ink test is very simple, but it clearly indicates the dynamics of CSF flow of mice. The ink is injected into the lateral ventricle, and reaches the deep cervical lymph nodes within a few minutes in normal mice. In mice with hrTGF-β1-induced hydrocephalus, there were no histological changes at the cribriform plate, but movement of the ink into the deep cervical lymph nodes took more than 10 minutes.

The method consists of injecting black ink into the lateral ventricle, to prevent leakage of the ink to the extra-cranium via a burr hole. In brief, the neck of the anesthetized mouse is opened and the deep cervical lymph nodes are exposed. Then, the mouse is placed in the stereotaxic frame, and 10 µl of black ink (particle size, 20-50 nm; Pelikan AG, Hanover, Germany) is injected into the lateral ventricle. After the ink injection, the deep cervical lymph nodes are examined to assess the color changes. The time it takes for the lymph nodes to turn black after the ink injection is recorded as the ink passage time. The mice are sacrificed for light and electron microscopic examinations after the test.

Computed Tomographic Cisternography

Pairs of anesthetized mice (one hydrocephalic and one normal in each pair) were examined with computed tomography (CT) cisternography. The times of the examinations were 15, 30, 45 and 60 minutes after intraventricular injection of 10 µl of 50% Iopamiron (Dai-ichi Pharma. Tokyo, Japan).

Light Microscopy

The brain was fixed with 10% buffered formaldehyde for histological examination. It was sectioned coronally, embedded in paraffin, and stained using hematoxylin/eosin (HE) and Malory-Azan methods.

Electron Microscopy

Specimens of meningeal tissue, from the area of convexity contralateral to the injection, were fixed in 2.5% glutaraldehyde, fixed again in 1% $OsO_4$ (osmium tetroxide), and then embedded in an Epon-Araldite mixture. Ultra-thin sections were stained with uranyl acetate and lead citrate, and then observed with a JEM-I200EX electron microscope (Nippon Electric Co., Tokyo, Japan).

Statistical Analysis

The data from the Morris water maze were expressed as mean±SEM. Statistical analysis of Morris water maze data was performed using a repeated measures analysis of variance (ANOVA) procedure. Post hoc comparisons were assessed using the Tukey—Kramer method. The other experimental results were presented as mean±S.D., and the statistical analysis was performed using paired or unpaired Student's t test. A P value of <0.05 indicated statistical significance.

Results: Hydrocephalic Mice

Twenty-five of the 44 TGF-β1-injected mice (56.7%) showed clear disturbance of spatial learning in the Morris water maze at 6 weeks after injection. This is significantly different from the results of 0.1% BSA-PBS-injected mice, in which 13 of the 14 mice showed clear deviation of their wake in quadrant A. Ventricular size of the 25 TGF-β1-injected mice with disturbed spatial learning was examined using MRI, and their ventricular size was compared with that of LAP-injected mice as a control. The ventricular sizes of the TGF-β1-injected mice and LAP-injected mice were 13.8±5.0% (n=25) and 5.9±1.8% (n=9), respectively; the difference was significant at the sixth week (p<0.005) (FIG. 1). The T2-weighted coronal brain images including thalamus were compared. The rate of high-intensity pixels indicating lateral and third ventricles among total pixels of the brain was defined as the ventricular size of the coronal section. Mice with disturbed spatial learning and ventriculomegaly were designated as hydrocephalic. Each upper image is a demonstrable image.

Subcutaneous fluid collection near the burr hole in the second MRI of 3 sham-operated hydrocephalus mice was also observed. This indicates that the CSF did not easily flow along the ordinal route, and leaked from the injecting hole of the cortex and the burr hole. Such abnormal fluid collection was not seen in any of the hrHGF-administered mice, indicating normalization of CSF flow.

Results: CT Cisternography

Figure 2:
FIG. 2 illustrates turnover of intraventricularly injected contrast material In normal and hydrocephalic mice.

To examine stasis of CSF flow in the hydrocephalic mice, CT cisternography of the hydrocephalic mice was performed. FIG. 2 shows the images taken at 30, 60, 90 and 120 minutes after intra-ventricular injection of the contrast material. A pair of hydrocephalic and normal mice was examined with computed tomography cisternography (CTC) after intra-ventricular injection of contrast material. In normal mice, the contrast material flowed beyond the frontal inter-hemispheric fissure within 30 mm (arrow), and was recycled in the whole body at 120 minutes; the whole body was enhanced well with the contrast material.

In the hydrocephalic mice, the contrast material stayed in the frontal inter-hemispheric fissure until 120 minutes (arrow). The intraventricularly injected contrast material clearly stayed in the interhemispheric fissure at least 120 minutes after injection in the hydrocephalic mice. These results strongly suggest that intermeningeal fibrosis is a main cause of hrTGF-β1-induced hydrocephalus.

Results: The Venticular Size in the Coronal Section

I. Administration of hrHGF for 14 Days with Model 1002 Infusion Pump

Figure 3:
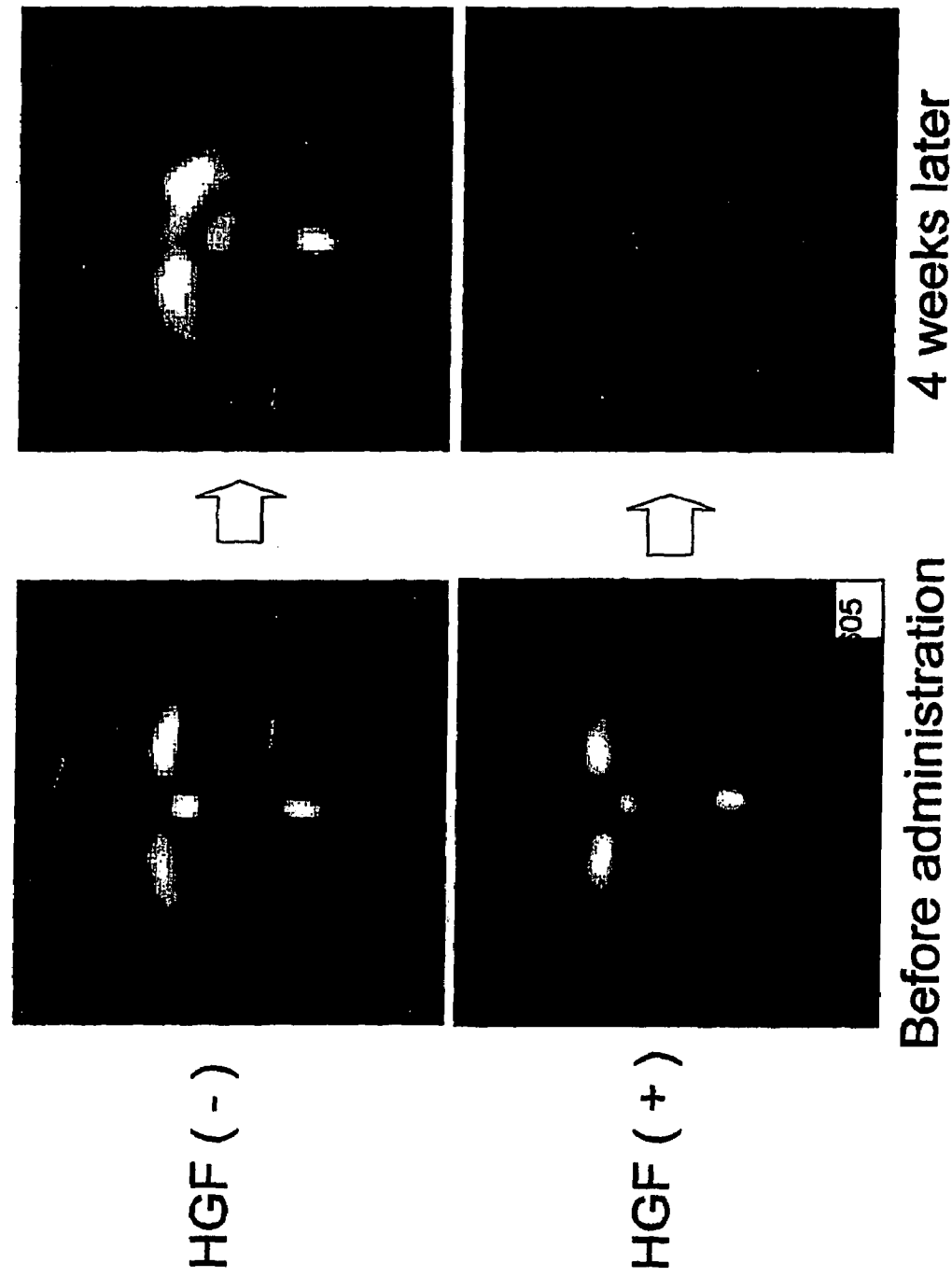
FIG. 3 depicts T2-weighted images of the coronal section of brain of hydrocephalic mice with and without administration of human recombinant (hr) HGF.

Five hydrocephalic mice were each administered 30 μg of hrHGF using a 14-day infusion pump. MRI showed that the ventricular size decreased from 10.7±2.5% before hrHGF administration to 7.4±2.1% at 4 weeks after the beginning of the HGF administration; this difference was significant (p<0.013). The lateral wall of the lateral ventricle became curved inward; the expanding shape of the lateral ventricle was clearly changed to a sunken shape. The tendency of decreasing ventricular size was in clear contrast to the 0.1% BSA-PBS-injected hydrocephalic mice (FIG. 3). By contrast, ventriculomegaly continued in hydrocephalic mice without administration of hrHGF.

II. Administration of hrHGF for 7 Days with Model 1007D Infusion Pump

Another 5 hydrocephalic mice were each administered 30 μg of hrHGF using a 7-day infusion pump. The ventricular size was 18.5±0.6% before hrHGF administration, and decreased to 15.3±2.9% at 4 weeks after the start of hrHGF administration. It tended to decrease, but this was not significant (p=0.085).

The pre- and post-ventricular sizes of the sham-operated hydrocephalic mice, which were injected with 0.1% BSA-PBS using a Model 1007D pump, were 13.8±5.0% and 13.8±4.8%, respectively. The ventricular size was not changed statistically, but the second MRI showed subcutaneous fluid collection near the burr hole in 3 of 7 mice. There was no such abnormal fluid collection in the HGF-administered mice (Table 1).

Results: Morris Water Maze

Figure 4:
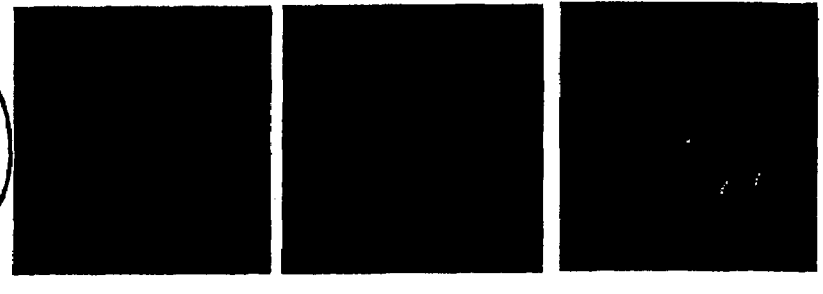
FIG. 4 illustrates the experimental design of Morris water maze and demonstrable wake of each mouse in the transfer test.
Figure 4:
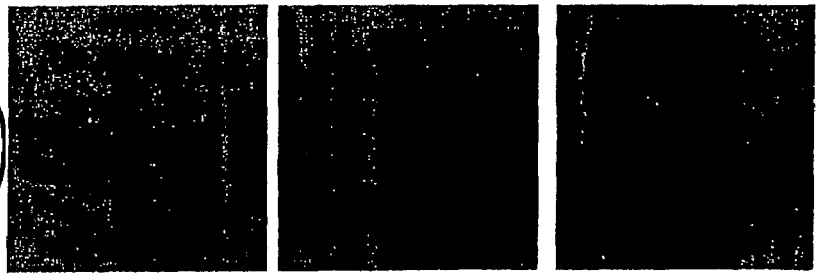

The sham-operated normal mice, which were injected with 0.1% BSA-PBS twice at an interval of 6 weeks, showed significant deviation of the wake in quadrant A in the first and second maze tests. The sham-operated hydrocephalic mice showed no deviation of the wake in any quadrant in either test. The hydrocephalic mice which were administered hrHGF using a 14-day osmotic pump also showed no deviation In any quadrant. The mice administered hrHGF using a 7-day osmotic pump which were showed no deviation of the wake in any quadrant before HGF administration, and completely recovered their spatial learning ability in the second test. FIG. 4 shows the demonstrable wakes of the same mice, and FIG. 5 shows the results of the transfer tests of all 5 mice.

With respect to FIG. 4, the second tests were performed 4 weeks after the start of human recombinant (hr) HGF administration. A is the quadrant of the pool in which the submerged platform was initially placed, and B, C and 0 are the remaining 3 quadrants, proceeding in a clockwise direction. Sham-operated normal mice showed a distinct laterality for swimming in quadrant A in both tests. The sham-operated (0.1% BSA-PBS injected) hydrocephalic mice showed no continuous quadrant laterality of their wakes. The hrHGF-administered hydrocephalic mice recovered spatial learning ability well in the second transfer test.

Figure 5:
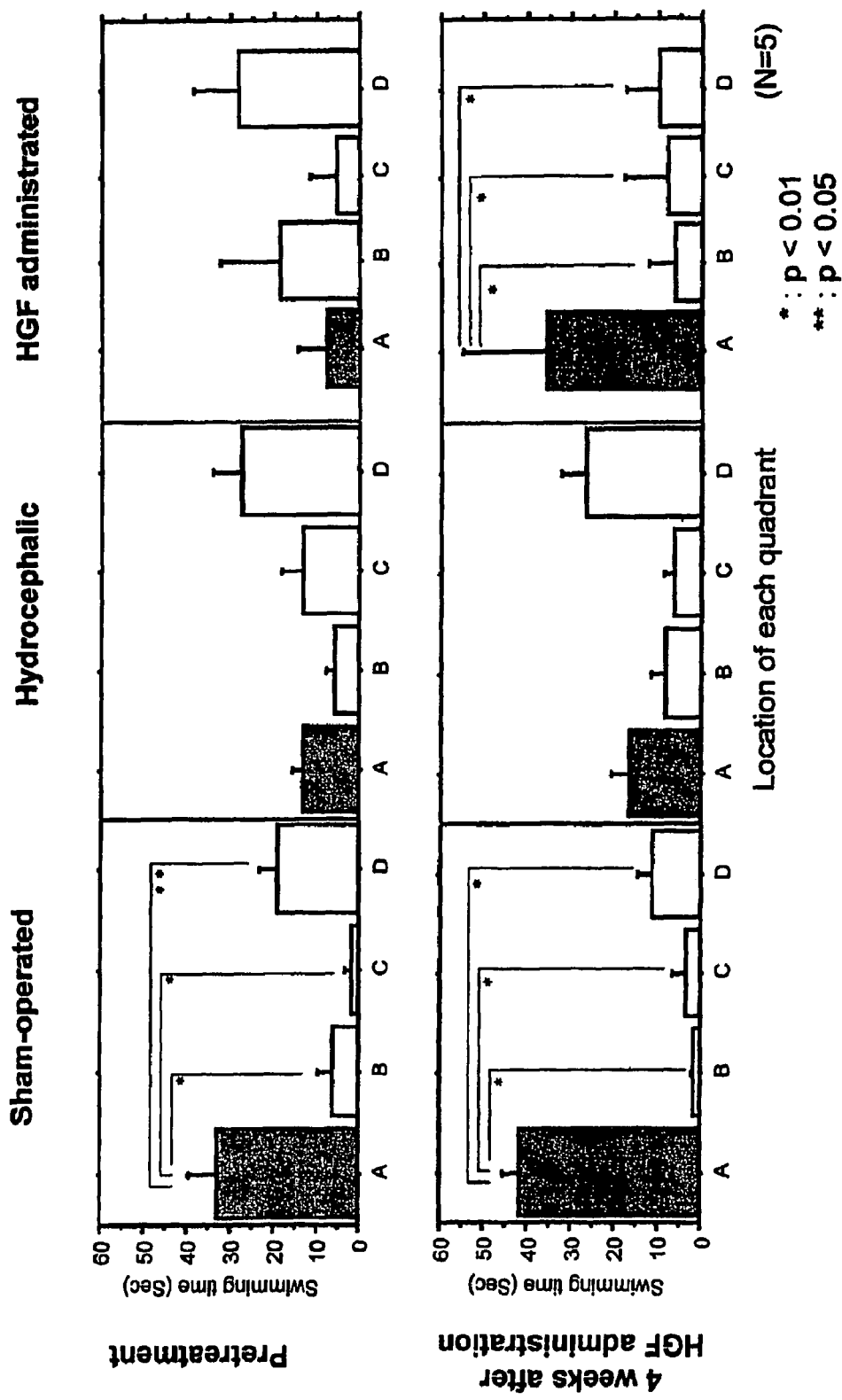
FIG. 5 depicts the results of transfer test of five hydrocephalic mice administered (hr) HGF using an osmotic infusion pump for 7 days. (A) is the quadrant in which the platform was placed, and the remaining quadrants, proceeding clockwise, are (B), (C), and (D) respectively.

With respect to FIG. 5, the mice were required to swim in the pool without the platform for 60 seconds. The time the mice spent swimming in each quadrant was measured as the score. The sham-operated normal mice, which were injected with 0.1% BSA-PBS twice at an interval of 6 weeks, showed fine spatial learning ability; deviation of wake in quadrant A, 2 times (n=5). The sham-operated

TABLE 1

| Administrated Materials | N | Duration of infusion (Days) | Ventricular Rate of Coronal Section | | P-value | Abnormal Fluid Collection |
| --- | --- | --- | --- | --- | --- | --- |
| | | | Pre administration | Post administration* | | |
| 0.1% BSA-PBS | 7 | 7 | 13.8 ± 5.0% | 13.8 ± 4.8% | 0.996 | Subcutaneous fluid collection (3)** |
| Human recombinant HGF | 5 | 7 | 18.5 ± 0.6% | 15.3 ± 2.9% | 0.085 | (−) |
| Human recombinant HGF | 5 | 14 | 10.7 ± 2.5% | 7.4 ± 2.1% | 0.013 | (−) |

*T2 weighted image of magnetic resonamce were taken after 4 weeks after the start of hr HGF administration
**Subcutaneous fluid collection above the burr hole was found in the second MRI of 3 sham-operated hydrocephalic mice hydrocephalic mice, which were injected with 0.1% BSA-PBS instead of human recombinant (hr) HGF, still had disturbed spatial learning at 4 weeks after administration (n=5). The hrHGF-administered hydrocephalic mice clearly recovered spatial learning ability.

Results: Ink Passage Time

Figure 6:
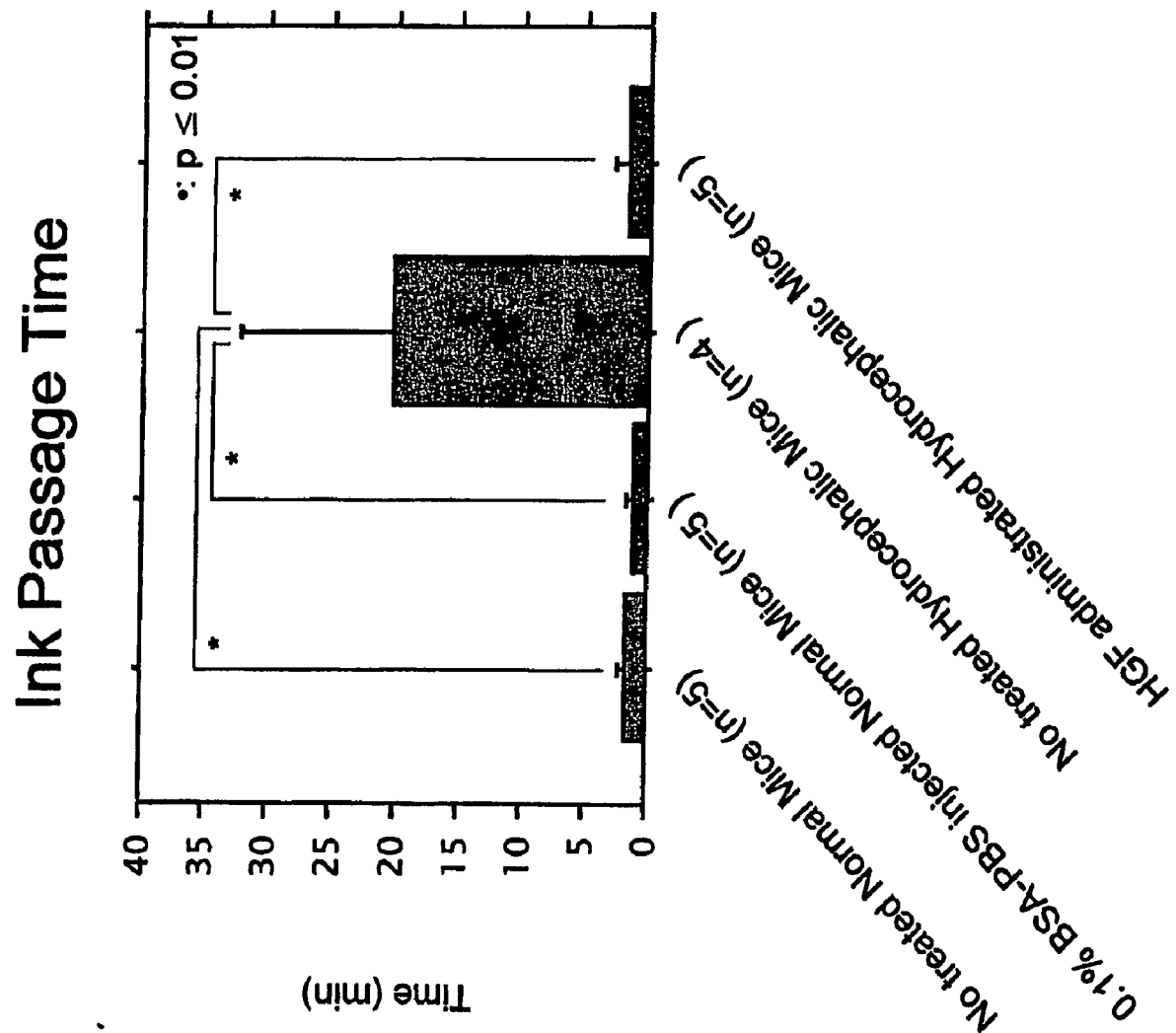
FIG. 6 is a histogram illustrating ink passage time across the various groups: non-treated normal mice (n=5); sham-operated (0.1% BSA-PBS injected) mice (n=5); hydrocephalic mice injected with 0.1% BSA-PBS with the 7-day osmotic pump (n=4); hydrocephalic mice, administered human recombinant HGF using the 7-day infusion pump (n=5).

Mouse CSF mainly drains to the nasal submucosal lymphatic ducts via the ethmoid foramen. The black ink (10 μl) was injected into the lateral ventricle, after the deep cervical lymph nodes were exposed. The time required for the lymph nodes to turn black after the beginning of the ink injection was recorded as the ink passage time. The ink passage time was 1.6±0.7 mm in the non-treated normal mice (n=5), and was 1.4±0.2 mm in sham-operated normal mice injected with 0.1% BSA-PBS twice at an interval of 6 weeks (n=5). In contrast, ink passage time was 20.3±12.1 minutes in the hydrocephalic mice that were injected with 0.1% BSA-PBS with the 7-day infusion pump (n=4). The time was 1.8±1.1 minutes in the hydrocephalic mice administered hrHGF using the 7-day infusion pump (n=5). The ink passage time of sham-operated hydrocephalic mice was longer than for other mice and was statistically significant (p≦0.01). The ink passage time completely normalized in mice administered hrHGF (FIG. 6).

Results: Histology

Figure 7:
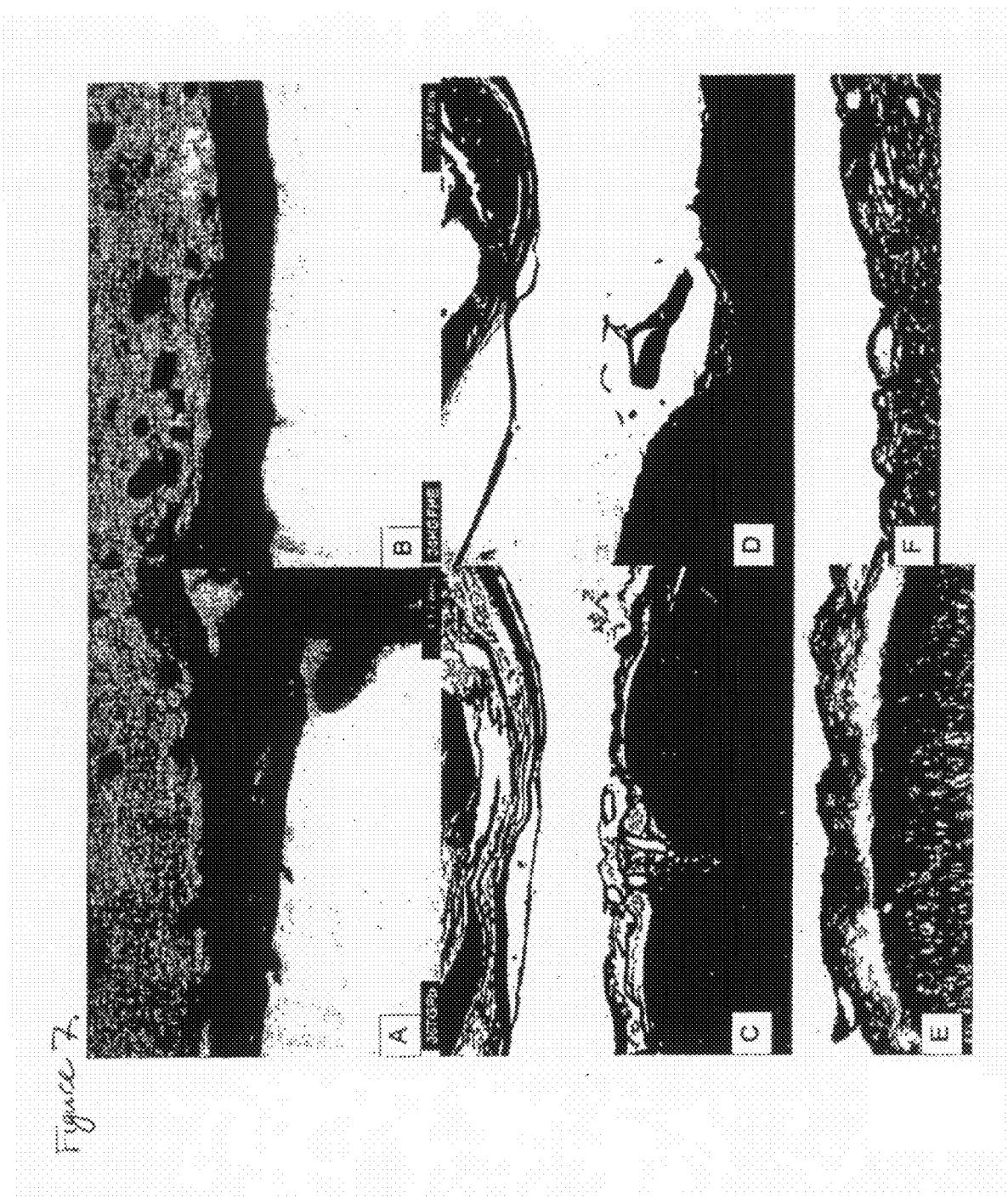
FIG. 7 depicts meningeal staining in hydrocephalic mice. (A) hematoxylin-eosin (HE) staining of meninges of the sham-operated hydrocephalic mice; (B) HE staining of meninges of (hr)-HGF-administered hydrocephalic mice; (C) Malory-Azan staining showed fibrous meninges around the brainstem of hydrocephalic mice compared with the hrHGF-administered hydrocephalic mice. (D) hrHGF-administered hydrocephalic mice shows clear reduction of collagen fibers in the meninges. (E, F) Magnification of the meningeal fibrosis at the brain stem (C, 0, respectively).

The meninges of ink-injected mice stained with HE showed apparent differences in distribution patterns of the carbon particles between sham-operated and hrHGF-administered mice. The meninges near the carotid artery of the sham-operated hydrocephalic mice showed clear localization of carbon black at the inside of the meninges (FIG. 7A). In contrast, meninges from a similar region in hrHGF-administered hydrocephalic mice showed wide distribution of black ink throughout the meningeal layer (FIG. 7B).

The Malory-Azan staining clearly showed a difference between hrHGF- and 0.1% BSAPBS-administered hydrocephalic mice. FIG. 7C, D shows the meninges surrounding the brain stem of the sham-operated and hrHGF-administered hydrocephalic mice, respectively. FIG. 7C demonstrates that the Malory-Azan staining showed fibrous meninges around the brainstem of hydrocephalic mice compared with the hrHGF-administered hydrocephalic mice. The hrHGF-administered hydrocephalic mice showed clear reduction of collagen fibers in the meninges (FIG. 7D). Collagen tissue in the meninges was clearly thinner in hrHGF-administered mice than in sham-operated hydrocephalic mice. FIGS. 7E, F are magnified images of the collagen tissue.

Figure 8:
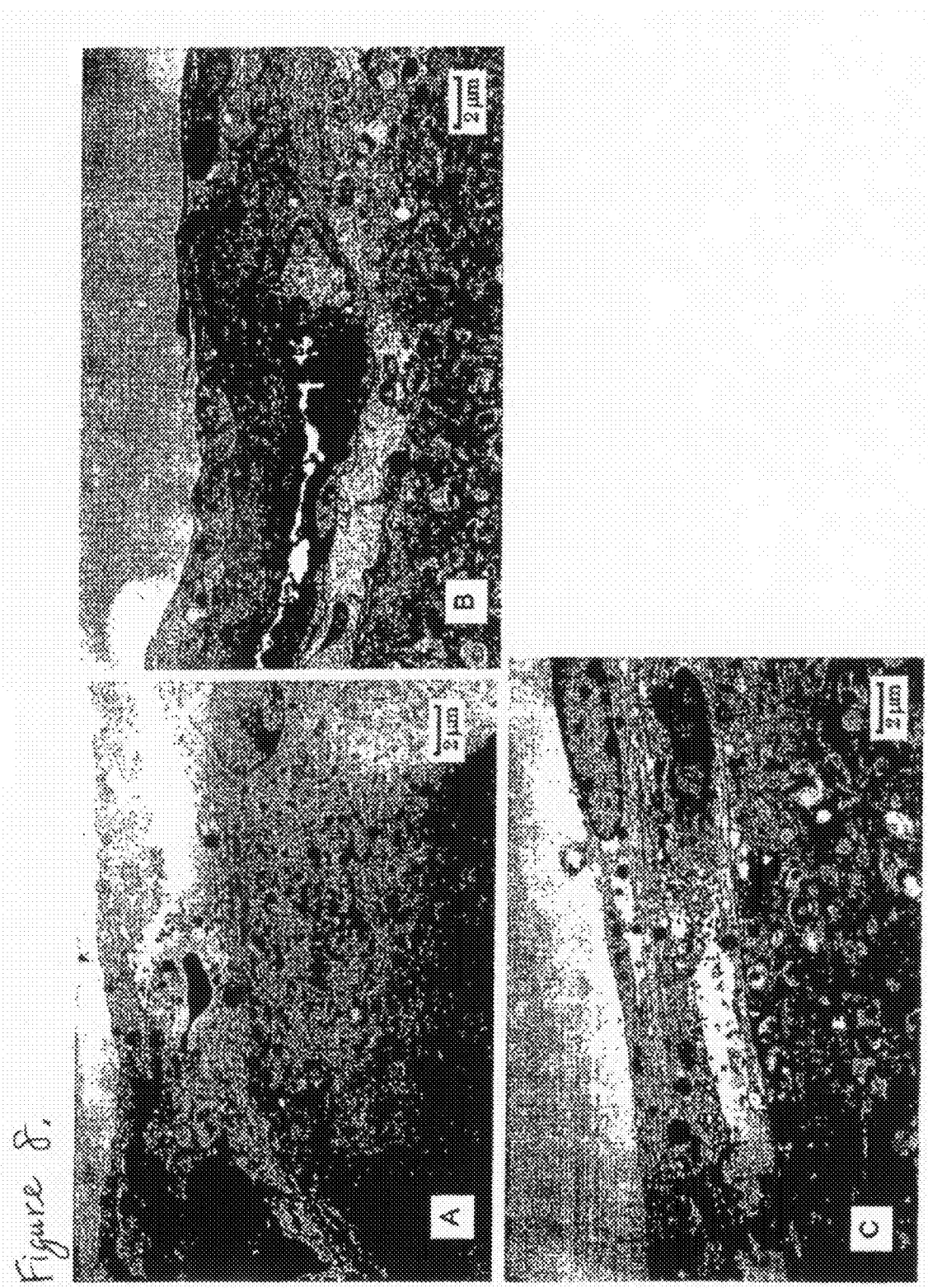
FIG. 8 shows electron microscopic images after ink passage test. (A) Meninges of sham-operated normal mouse; (B) Meninges of the hydrocephalic mice; (C) Meninges of the hrHGF-administered hydrocephalic mice.

FIG. 8A shows normal mouse meningeal cells at the electron microscopic level after the ink injection test. The meningeal cells had thin cytoplasmic processes, which formed lamellar structures in the meninges. Many carbon particles were observed in the intermeningeal cellular space. Some of the carbon particles were phagocytized by macrophages that migrated into the space. The electron microscopic examination also showed differences between the hrHGF-administered and sham-operated hydrocephalic mice after the ink test. FIG. 8B shows meninges obtained from a sham-operated hydrocephalic mouse. There was apparent increase in cellularity of the meningeal tissue; intercellular space was absent in the meninges; and Ink particles were difficult to detect. In contrast, the meninges obtained from the hrHGF-administered hydrocephalic mice showed a lamellar structure of meningeal cells that was very similar to that of the sham-operated normal mice; many carbon particles were observed in the inter-meningeal cellular space (FIG. 8C).

It is believed that the present results are useful for considerations including the development of a clinical trial of recombinant HGF treatment in human hydrocephalus.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

What is claimed is:

1. A method of treating communicating hydrocephalus in an animal or a human, comprising administering intraventricularly a pharmaceutical composition comprising human recombinant hepatocyte growth factor (hrHGF) to an animal or human in need thereof.

2. The method of claim 1, wherein the pharmaceutical composition further comprises a pharmaceutically acceptable carrier.

3. The method of claim 2, wherein the pharmaceutically acceptable carrier is at least one selected from the group consisting of a carrier material, diluent, excipient, wetting agent, buffering agent, suspending agent, lubricating agent, adjuvant, vehicle, and material for delivery system.

4. The method of claim 2, wherein the pharmaceutically acceptable carrier is a carrier material for administering the HGF into a route of cerebrospinal fluid (CSF).

* * * * *